(12) United States Patent
Hodous et al.

(10) Patent No.: US 8,236,823 B2
(45) Date of Patent: Aug. 7, 2012

(54) MULTI-CYCLIC COMPOUNDS AND METHODS OF USE

(75) Inventors: Brian L. Hodous, Cambridge, MA (US); Stephanie D. Geuns-Meyer, Medford, MA (US); Philip R. Olivieri, Charlestown, MA (US); Vinod F. Patel, Acton, MA (US)

(73) Assignee: Amgen Inc., Thousand Oaks, CA (US)

( * ) Notice: Subject to any disclaimer, the term of this patent is extended or adjusted under 35 U.S.C. 154(b) by 1153 days.

(21) Appl. No.: 11/977,970

(22) Filed: Oct. 25, 2007

(65) Prior Publication Data

US 2008/0255205 A1    Oct. 16, 2008

Related U.S. Application Data

(60) Provisional application No. 60/863,172, filed on Oct. 27, 2006.

(51) Int. Cl.
*A61K 31/4439* (2006.01)
*C07D 401/04* (2006.01)

(52) U.S. Cl. .............. 514/341; 546/275.4; 546/276.1

(58) Field of Classification Search .......... 546/275.4, 546/276.1; 514/341
See application file for complete search history.

(56) References Cited

U.S. PATENT DOCUMENTS

| 6,395,733 | B1 | 5/2002 | Arnold |
| 6,465,449 | B1 | 10/2002 | Kath |
| 6,919,338 | B2 | 7/2005 | Mortlock |
| 7,135,550 | B2 | 11/2006 | Come |
| 7,868,177 | B2 * | 1/2011 | Cee et al. .......... 546/268.1 |
| 7,880,000 | B2 | 2/2011 | Geuns-Meyer |
| 2003/0018029 | A1 | 1/2003 | Barker |

FOREIGN PATENT DOCUMENTS

| WO | 03/005491 A1 | 7/2003 |
| WO | 2004/000833 A1 | 12/2003 |
| WO | 2004/013141 A1 | 2/2004 |
| WO | 2004/016612 A2 | 2/2004 |
| WO | 2004/030635 A2 | 4/2004 |
| WO | 2004/037814 A1 | 5/2004 |
| WO | 2004/039774 A2 | 5/2004 |
| WO | 2004/052280 A2 | 6/2004 |
| WO | 2004/054585 A1 | 7/2004 |
| WO | 2005/033086 A1 | 4/2005 |
| WO | 2005/042520 A1 | 5/2005 |

OTHER PUBLICATIONS

R. Giet and C. Prigent, J. Cell. Sci., 112:3591-3601 (1999).
Y. Miyoshi et al., Int. J. Cancer, 92:370-373 (2001).
Berge et al., J. Pharm. Sci., 66, 1 (1977).

* cited by examiner

*Primary Examiner* — Patricia Morris
(74) *Attorney, Agent, or Firm* — G. Prabhakar Reddy

(57) ABSTRACT

The present invention relates to compounds of Formulas I and II,

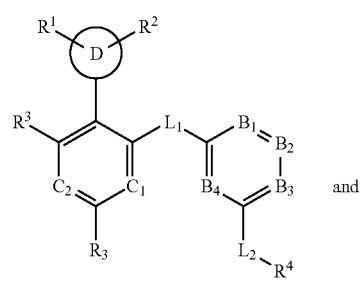

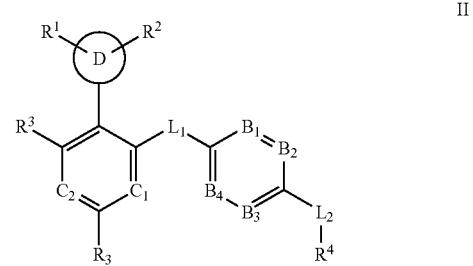

wherein $B^1$, $B^2$, $B^3$, $B^4$, $C^1$, $C^2$, ring D, $L^1$, $L^2$ and $R^{1-4}$ are defined herein, synthetic intermediates, and pharmaceutical compositions, comprising such compounds. The compounds and compositions are capable of modulating various protein kinase receptors such as Tie-2 and Aurora and, therefore, influencing kinase related disease states and conditions. The compounds, for example, are capable of treating cancer caused by unregulated angiogenesis, and inflammation as well as other proliferative disorders.

13 Claims, No Drawings

MULTI-CYCLIC COMPOUNDS AND METHODS OF USE

This application claims the benefit of U.S. Provisional Application No. 60/863,172, filed Oct. 27, 2006, which is hereby incorporated by reference.

FIELD OF THE INVENTION

The invention generally relates to the field of pharmaceutical agents and, more specifically, to compounds, intermediates, methods for making the compounds and intermediates, compositions, uses and methods for modulating Tie-2 and/or Aurora kinases and for treating diseases related thereto.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Examples of kinases in the protein kinase family include, without limitation, ab1, Akt, Aurora A, Aurora B, Aurora C, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, Tie, Tie2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating cell proliferation, activation, and/or differentiation. Uncontrolled or excessive kinase activity has been observed in many disease states including benign and malignant proliferation disorders as well as diseases resulting from inappropriate activation of the immune system (autoimmune disorders), allograff rejection, and graft vs host disease. In addition, endothelial cell specific receptor PTKs, such as Tie-2, mediate the angiogenic process and are involved in supporting the progression of cancers and other diseases involving uncontrolled vascularization.

Angiogenesis is the process of developing new blood vessels, particularly capillaries, from pre-existing vasculature and is an essential component of embryogenesis, normal physiological growth, repair, and tumor expansion. Angiogenesis remodels small vessels into larger conduit vessels, a physiologically important aspect of vascular growth in adult tissues. Vascular growth is required for beneficial processes such as tissue repair, wound healing, recovery from tissue ischemia and menstrual cycling.

Certain diseases and/or pathological conditions develop as a result of, or are known to be associated with, the regulation and/or deregulation of angiogenesis. For example, ocular neovascularisation such as retinopathies (including diabetic retinopathy), age-related macular degeneration, psoriasis, hemangioblastoma, hemangioma, and arteriosclerosis have been found to be caused, in part, due the loss of regulation and/or maintenance of vascular growth. Inflammatory diseases such as a rheumatoid or rheumatic inflammatory disease, and especially arthritis (including rheumatoid arthritis) where new capillary blood vessels invade the joint and destroy cartilage, have been associated with angiogenesis. In addition, chronic inflammatory disorders such as chronic asthma, arterial or post-transplantational atherosclerosis, endometriosis, and neoplastic diseases including so-called solid tumors and liquid tumors (for example, leukemias), have been found to be linked to the regulation and control of angiogenesis.

The involvement of angiogenesis in major diseases has led to the identification and development of various targets for inhibiting angiogenesis. One target identified in the cascade of events leading to angiogenesis is the Tie receptor family. The Tie-1 and Tie-2 receptors are single-transmembrane, tyrosine kinase receptors (Tie stands for tyrosine kinase receptors with immunoglobulin and EGF homology domains). Tie-2 is an endothelial cell specific receptor tyrosine kinase, which is involved in angiogenic processes, such as vessel branching, sprouting, remodeling, maturation and stability. Tie-2 is the first mammalian receptor for which both agonist ligand(s) (for example, Angiopoietin-1 ("Ang1") which binds to and stimulates phosphorylation and signal transduction of Tie-2), and context dependent agonist/antagonist ligand(s) (for example, Angiopoietin-2 ("Ang2")) have been identified. Knock out and transgenic manipulation of the expression of Tie-2 and its ligands indicates that tight spacial and temporal control of Tie-2 signaling is important for the proper development of new vascularization.

Biological models suggest that the stimulation of Tie-2 by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial death, especially in the absence of growth/survival stimuli.

Recently, upregulation of Tie-2 expression has been found in the vascular synovial pannus of arthritic joints of humans, consistent with the role in inappropriate neovasculariation. This finding suggests that Tie-2 plays a role in the progression of rheumatoid arthritis. Point mutations producing constitutively activated forms of Tie-2 have been identified in association with human venous malformation disorders. Tie-2 inhibitors would, therefore, be useful in treating such disorders, as well as in other instances of improper neovasacularization. However, with the recent recognition of Ang3 and Ang4 as additional Tie-2 binding ligands, targeting a Tie-2 ligand-receptor interaction as an anti-angiogenic therapeutic approach is less favorable. Accordingly, a Tie-2 receptor kinase inhibition approach has become the strategy of choice.

The inhibition of vascular growth in this context has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Regulating angiogenesis by inhibiting certain recognized pathways in this process would, therefore, be useful in treating diseases, such as ocular neovascularization, including retinopathy, age-related macular degeneration, psoriasis, hemangioblastoma, hemangioma, arteriosclerosis, inflammatory disease rheumatoid arthritis, chronic inflammatory disorders such as chronic asthma, arterial or post-transplantational atherosclerosis, endometriosis, and neoplastic diseases such as leukemias, otherwise known to be associated with deregulated angiogenesis.

Another mechanism by which cancerous cells are propagated is by unregulated cell proliferation. Damage to one or more genes, responsible for the cellular pathways, which control progress of proliferation through the cell cycle, typically causes the loss of normal regulation of cell proliferation. These genes code for various proteins, which participate in a cascade of events, including protein phosphorylation, leading to cell-cycling progression and cell proliferation.

One class of proteins found to play a part in cell cycling and, therefore, cell proliferation is the Aurora kinase family of proteins. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also commonly referred to as Aurora 1, Aurora 2, and Aurora 3, respectively.

The specific function of each Aurora kinase member in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases appear to be viable targets for the treatment of cancer. Aurora kinases are overexpressed in various types of cancers, including colon, breast, lung, pancrease, prostate, bladder, head, neck, cervix, and ovarion cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)). Further, inhibition of Aurora has been found to arrest cell cycling and promote programmed cell death via apoptosis. Accordingly, there has been a strong interest in finding inhibitors of Aurora kinase proteins.

Many classes of compounds have been proposed to treat cancerous conditions and disorders, including publications disclosing compounds to modulate or specifically inhibit Tie-2 or Aurora kinase activity. For example, WO 04/030635 describes various classes of compounds as vasculostatic agents; WO 04/013141 describes condense pyridines and pyrimidines with Tie-2 activity; WO 04/054585 describes anilino-substituted heterocyclic compounds for the treatment of abnormal cell growth; U.S. Pat. No. 6,395,733 describes heterocyclic ring-fused pyrimidine derivatives, useful in the treatment of hyperpoliferative diseases; U.S. Pat. No. 6,465,449 describes heteroaromatic bicyclic derivatives useful as anticancer agents; U.S. Patent Publication No. 2003/0018029 describes heterocyclic compounds useful in the treatment of poliferative diseases such as cancer; WO 04/039774 describes aza-quinazolinones for treating cancer via inhibition of Aurora kinase; WO 04/037814 describes indazolinones for treating cancer via inhibition of Aurora-2 kinase; WO 04/016612 describes 2, 6, 9-substituted purine derivatives for treating cancer via inhibiton of Aurora kinase; WO 04/000833 describes tri- and tetra-substituted pyrimidine compounds useful for treating Aurora-mediated diseases; WO 04/092607 describes crystals useful for screening, designing and evaluating compounds as agonists or antagonists of Aurora kinase and U.S. Pat. No. 6,919,338 and WO 03/055491 each describe substituted quinazoline derivatives as inhibitors of Aurora-2 kinase. Inspite of the current attempts at finding an anti-cancer therapeutic, there remains a need to find improved, more effective anti-cancer therapies.

BRIEF DESCRIPTION OF THE INVENTION

The present invention provides new multi-cyclic compounds useful in treating cancer, inflammation and related disorders and conditions. In particular, the compounds are useful for treating pathological conditions and/or disease states related to Tie-2 and/or Aurora kinase activity. The compounds are useful by virtue of their ability to regulate active angiogenesis, cell-signal transduction and related pathways, for example, through kinase modulation. The compounds provided by the invention, including stereoisomers, tautomers, solvates, pharmaceutically acceptable salts, derivatives or prodrugs thereof, are defined by general Formula I and by Formula II

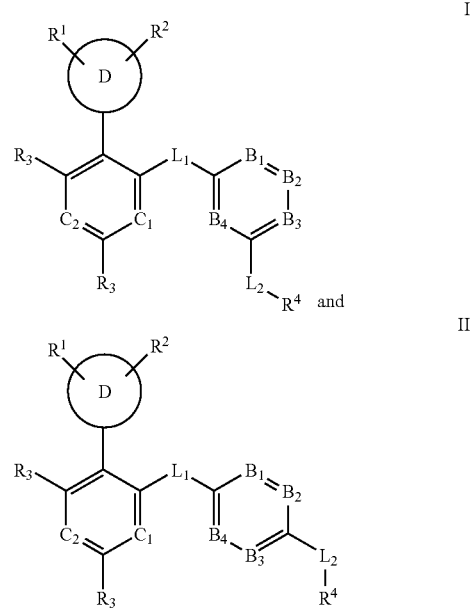

wherein $B^1$, $B^2$, $B^3$, $B^4$, $C^1$, $C^2$, ring D, $L^1$, $L^2$ and $R^{14}$ of Formulas I and II are as described herein below.

The invention also provides procedures for making compounds of Formula I and Formula II, as well as intermediates useful in such procedures.

The invention further provides for the use of these compounds for the preparation of a pharmaceutical composition or medicament, useful to attenuate, alleviate, or treat angiogenesis- or cell proliferation-mediated diseases, including tumors and other cancerous conditions, through inhibition of Tie-2 and/or Aurora kinase.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the present invention, multi-cyclic compounds of Formulas I, including stereoisomers, tautomers, solvates, pharmaceutically acceptable salts, derivatives or prodrugs thereof, are defined by general Formula I:

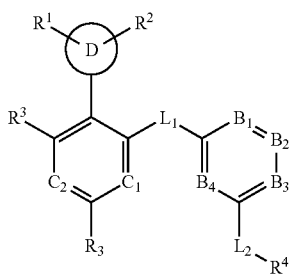

I wherein each of $B^1$, $B^2$, $B^3$ and $B^4$, independently, is $CR^3$ or N, provided that no more than two of $B^1$, $B^2$, $B^3$ and $B^4$ is N;

each of $C^1$ and $C^2$, independently, is $CR^3$ or N;

ring D is a 5-membered heteroaryl ring formed of carbon atoms and having at least one heteroatom selected from N, O and S and wherein one or more of $R^1$ and $R^2$ may be absent when said D ring has no monovalent carbon atoms;

$L^1$ is $NR^3$, O, S, C(O), S(O), $SO_2$ or $CR^3R^3$;

$L^2$ is —C(O)—, —S(O)$_2$—, —NR—, —(CR$^3$R$^3$)$_n$C(O)NR$^3$—, —COO—, —(CR$^3$R$^3$)$_n$NR$^3$C(O)—, —(CR$^3$R$^3$)$_n$S(O)$_2$NR$^3$— or —NR$^3$S(O)$_2$—;

$R^1$ is H, $C_{1-10}$-alkyl, $C_{2-10}$-alkenyl, $C_{2-10}$-alkynyl or $C_{3-7}$-cycloalkyl, each of the $C_{1-10}$-alkyl, $C_{2-10}$-alkenyl, $C_{2-10}$-alkynyl and $C_{3-7}$-cycloalkyl optionally substituted with one or more substituents of $R^6$, or $R^1$ is $R^6$;

$R^2$ is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl;

each $R^3$, independently, is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl, the $C_{1-10}$-alkyl optionally comprising 1-3 heteroatoms selected from N, O and S and optionally substituted with one or more substituents of $R^5$ or $R^6$;

$R^4$ is $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-3 heteroatoms selected from N, O and S and optionally substituted with one or more substituents of $R^5$ or $R^6$; or $R^4$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^5$, $R^6$, oxo, NR$^6$R$^6$, OR$^6$, SR$^6$, C(O)R$^6$, COOR$^6$, C(O)NR$^6$R$^6$, NR$^6$C(O)R$^6$, NR$^6$C(O)NR$^6$R$^6$, OC(O)NR$^6$R$^6$, S(O)$_2$R$^6$, S(O)$_2$NR$^6$R$^6$ or NR$^6$S(O)$_2$R$^6$;

$R^5$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^6$, oxo, NR$^6$R$^6$, OR$^6$, SR$^6$, C(O)R$^6$, COOR$^6$, C(O)NR$^6$R$^6$, NR$^6$C(O)R$^6$, NR$^6$C(O)NR$^6$R$^6$, OC(O)NR$^6$R$^6$, S(O)$_2$R$^6$, S(O)$_2$NR$^6$R$^6$ or NR$^6$S(O)$_2$R$^6$;

each $R^6$, independently, is H, oxo, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1 or 2;

provided that (1) $R^4$ is not an optionally substituted benzothiophene ring, or (2) when ring D is a tetrazole, then both of $C^1$ and $C^2$ are not N, or (3) when ring D is a tetrazole, then $L^2$ is not —CH$_2$NR$^3$C(O)— when $R^4$ is phenyl, or (4) when ring D is a tetrazole, then $L^2$ is not —C(O)—.

Accordingly, the compounds encompassed in Formula I do not include (1) those compounds having $R^4$ as an optionally substituted benzothiophene ring, regardless of what the substitutions may be, or (2) those compounds having ring D as a tetrazole and both of $C^1$ and $C^2$ as N, or (3) those compounds having ring D as a tetrazole, $R^4$ as a phenyl and $L^2$ as —CH$_2$NR$^3$C(O)—, or (4) those compounds having ring D as a tetrazole and $L^2$ as a —C(O)—.

In another embodiment, the compounds, including stereoisomers, tautomers, solvates, pharmaceutically acceptable salts, derivatives or prodrugs thereof, are defined by general Formula II:

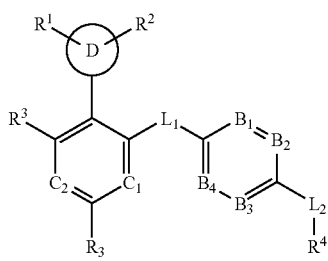

II or stereoisomer, tautomer, solvate, pharmaceutically acceptable salt, derivative or prodrug thereof, wherein each of $B^1$, $B^2$, $B^3$ and $B^4$, independently, is $CR^3$ or N, provided that no more than two of $B^1$, $B^2$, $B^3$ and $B^4$ is N;

each of $C^1$ and $C^2$, independently, is $CR^3$ or N;

ring D is a 5-membered heteroaryl ring formed of carbon atoms and having at least one heteroatom selected from N, O and S and wherein one or more of $R^1$ and $R^2$ may be absent when said D ring has no monovalent carbon atoms;

$L^1$ is $NR^3$, O, S, C(O), S(O), $SO_2$ or $CR^3R^3$;

$L^2$ is —C(O)—, —S(O)$_2$—, —$NR^3$—, —$(CR^3R^3)_nC(O)$ $NR^3$—, —COO—, —$(CR^3R^3)_nNR^3C(O)$—, —$(CR^3R^3)_nS(O)_2NR^3$— or —$NR^3S(O)_2$—;

$R^1$ is H, $C_{1-10}$-alkyl, $C_{2-10}$-alkenyl, $C_{2-10}$-alkynyl or $C_{3-7}$-cycloalkyl, each of the $C_{1-10}$-alkyl, $C_{2-10}$-alkenyl, $C_{2-10}$-alkynyl and $C_{3-7}$-cycloalkyl optionally substituted with one or more substituents of $R^6$, or $R^1$ is $R^6$;

$R^2$ is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl;

each $R^3$, independently, is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl, the $C_{1-10}$-alkyl optionally comprising 1-3 heteroatoms selected from N, O and S and optionally substituted with one or more substituents of $R^5$ or $R^6$;

$R^4$ is $C_{1-10}$-alkyl, $C_{2-10}$-alkenyl or $C_{2-10}$-alkynyl, each of the $Cl_{1-10}$-alkyl, $C_{2-10}$-alkenyl and $C_{2-10}$-alkynyl optionally comprising 1-3 heteroatoms selected from N, O and S and optionally substituted with one or more substituents of $R^5$ or $R^6$; or $R^4$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^5$, $R^6$, oxo, $NR^6R^6$, $OR^6$, $SR^6$, $C(O)R^6$, $COOR^6$, $C(O)NR^6R^6$, $NR^6C(O)R^6$, $NR^6C(O)NR^6R^6$, $OC(O)NR^6R^6$, $S(O)_2R^6$, $S(O)_2NR^6R^6$ or $NR^6S(O)_2R^6$;

$R^5$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^6$, oxo, $NR^6R^6$, $OR^6$, $SR^6$, $C(O)R^6$, $COOR^6$, $C(O)NR^6$, $R^6$, $NR^6C(O)R^6$, $NR^6C(O)NR^6R^6$, $OC(O)NR^6R^6$, $S(O)_2R^6$, $S(O)_2NR^6R^6$ or $NR^6S(O)_2R^6$;

each $R^6$, independently, is H, oxo, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1 or 2;

provided that (1) $R^4$ is not an optionally substituted benzothiophene ring, or (2) when ring D is a tetrazole, then both of $C^1$ and $C^2$ are not N, or (3) when ring D is a tetrazole, then $L^2$ is not —$CH_2NR^3C(O)$— when $R^4$ is phenyl, or (4) when ring D is an oxadiazole, $L^2$ is —NH— and both of $C^1$ and $C^2$ are CH, then $R^4$ is not a 10-membered heteroaryl ring, or (5) when ring D is a tetrazole, then $L^2$ is not —C(O)—.

Accordingly, the compounds encompassed in Formula II do not include (1) those compounds having $R^4$ as an optionally substituted benzothiophene ring, regardless of what the substitutions may be, or (2) those compounds having ring D as a tetrazole and both of $C^1$ and $C^2$ as N, or (3) those compounds having ring D as a tetrazole, $R^4$ as a phenyl and $L^2$ as —$CH_2NR^3C(O)$—, or (4) those compounds having ring D as an oxadiazole, $L^2$ as —NH— and both of $C^1$ and $C^2$ as CH, and $R^4$ as a 10-membered heteroaryl ring, or (5) those compounds having ring D as a tetrazole and $L^2$ as a —C(O)—.

In another embodiment, the invention provides compounds of Formulas I or II wherein each of $B^1$, $B^2$, $B^3$ and $B^4$, independently, is $CR^3$ or N, in conjunction with any of the above or below embodiments.

In another embodiment, the invention provides compounds of Formulas I or II wherein each of $B^1$, $B^2$, $B^3$ and $B^4$, independently, is $CR^3$, in conjunction with any of the above or below embodiments.

In another embodiment, the invention provides compounds of Formulas I or II wherein one of $B^1$, $B^2$, $B^3$ and $B^4$, independently, is N, in conjunction with any of the above or below embodiments.

In another embodiment, the invention provides compounds of Formulas I or II wherein no more than two of $B^1$, $B^2$, $B^3$ and $B^4$, independently, is N, in conjunction with any of the above or below embodiments.

In another embodiment, the invention provides compounds of Formulas I or II wherein one of $C^1$ is N and $C^2$ is CH, in conjunction with any of the above or below embodiments.

In another embodiment, the invention provide compounds of Formulas I or II wherein one of $C^1$ is CH and $C^2$ is N, in conjunction with any of the above or below embodiments.

In another embodiment, the invention provides compounds of Formulas I or II wherein each of $C^1$ and $C^2$, independently, is CH, in conjunction with any of the above or below embodiments.

In another embodiment, the invention provides compounds of Formulas I or II wherein each of $C^1$ and $C^2$, independently, is N, in conjunction with any of the above or below embodiments.

In another embodiment, the invention provides compounds of Formulas I or II wherein ring D is a 5-membered heteroaryl ring formed of carbon atoms and having at least one heteroatom selected from N, O and S and wherein one or more of $R^1$ and $R^2$ may be absent when said D ring has no monovalent carbon atoms, in conjunction with any of the above or below embodiments.

In another embodiment, the invention provide compounds of Formulas I or II wherein D is an optionally substituted ring selected from

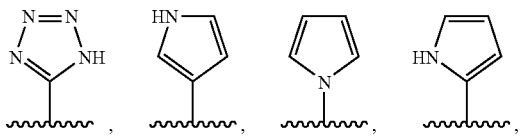

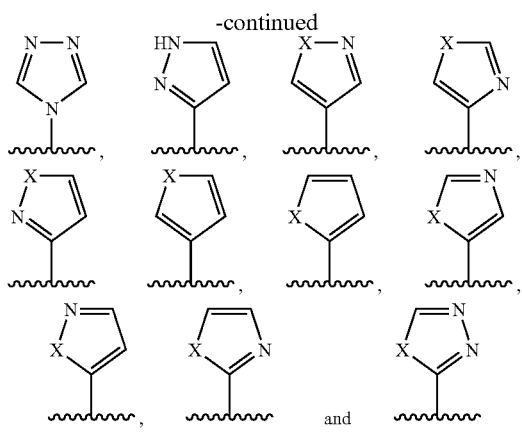

wherein X is NR$^6$, O or S, in conjunction with any of the above or below embodiments.

In another embodiment, the invention provides compounds of Formulas I or II wherein L$^1$ is NR$^3$, in conjunction with any of the above or below embodiments.

In another embodiment, the invention provides compounds of Formulas I or II wherein L$^1$ is O or S, in conjunction with any of the above or below embodiments.

In another embodiment, the invention provides compounds of Formulas I or II wherein L$^1$ is C(O), in conjunction with any of the above or below embodiments.

In another embodiment, the invention provides compounds of Formulas I or II wherein L$^1$ is S(O) or SO$_2$, in conjunction with any of the above or below embodiments.

In another embodiment, the invention provides compounds of Formulas I or II wherein L$^1$ is CR$^3$R$^3$, in conjunction with any of the above or below embodiments.

In another embodiment, the invention provide compounds of Formulas I or II wherein L$^2$ is —NR$^3$—, in conjunction with any of the above or below embodiments.

In another embodiment, the invention provides compounds of Formulas I or II wherein L$^2$ is —(CR$^3$R$^3$)$_n$C(O)NR$^3$— wherein n is 0, 1 or 2, in conjunction with any of the above or below embodiments.

In another embodiment, the invention provides compounds of Formulas I or II wherein L$^2$ is —(CR$^3$R$^3$)$_n$NR$^3$C(O)— wherein n is 0, 1 or 2, in conjunction with any of the above or below embodiments.

In another embodiment, the invention provides compounds of Formulas I or II wherein L$^2$ is —C(O)NR$^3$— or —NR$^3$C(O)—, in conjunction with any of the above or below embodiments.

In another embodiment, the invention provides compounds of Formulas I or II wherein L$^2$ is —C(O)NR$^3$—, —NR$^3$C(O)—, —NR$^3$S(O)$_2$— or —S(O)$_2$NR$^3$—, in conjunction with any of the above or below embodiments.

In another embodiment, the invention provides compounds of Formulas I or II wherein L$^2$ is —C(O)—, in conjunction with any of the above or below embodiments.

In another embodiment, the invention provides compounds of Formulas I or II wherein L$^2$ is —S(O)$_2$—, in conjunction with any of the above or below embodiments.

In another embodiment, the invention provides compounds of Formulas I or II wherein L$^2$ is —COO—, in conjunction with any of the above or below embodiments.

In another embodiment, the invention provides compounds of Formulas I or II wherein L$^2$ is —NR$^3$S(O)$_2$—, in conjunction with any of the above or below embodiments.

In another embodiment, the invention provides compounds of Formulas I or II wherein R$^1$ is H, C$_{1-10}$-alkyl, C$_{2-10}$-alkenyl, C$_{2-10}$-alkynyl or C$_{3-7}$-cycloalkyl, each of the C$_{1-10}$-alkyl, C$_{2-10}$-alkenyl, C$_{2-10}$-alkynyl and C$_{3-7}$-cycloalkyl optionally substituted with one or more substituents of R$^6$, or R$^1$ is R$^6$, in conjunction with any of the above or below embodiments.

In another embodiment, the invention provides compounds of Formulas I or II wherein R$^1$ is H, in conjunction with any of the above or below embodiments.

In another embodiment, the invention provides compounds of Formulas I or II wherein R$^1$ is C$_{1-10}$-alkyl, optionally substituted with one or more substituents of R$^6$, in conjunction with any of the above or below embodiments.

In another embodiment, the invention provides compounds of Formulas I or II wherein R$^1$ is R$^6$, in conjunction with any of the above or below embodiments.

In another embodiment, the invention provides compounds of Formulas I or II wherein R$^2$ is H, C$_{1-10}$-alkyl, halo, CN, haloalkyl, NO$_2$, NH$_2$, —NH—C$_{1-10}$-alkyl, —N-di-C$_{1-10}$-alkyl, OH or —O—C$_{1-10}$-alkyl, in conjunction with any of the above or below embodiments.

In another embodiment, the invention provides compounds of Formulas I or II wherein R$^2$ is H, C$_{1-10}$-alkyl, halo, CN, haloalkyl, NO$_2$, NH$_2$, —NH—C$_{1-10}$-alkyl, —N-di-C$_{1-10}$-alkyl, OH or —O—C$_{1-10}$-alkyl, in conjunction with any of the above or below embodiments.

In another embodiment, the invention provides compounds of Formulas I or II wherein R$^2$ is H, in conjunction with any of the above or below embodiments.

In another embodiment, the invention provides compounds of Formulas I or II wherein R$^2$ is C$_{1-10}$-alkyl, halo, CN, haloalkyl, NO$_2$, NH$_2$, —NH—C$_{1-10}$-alkyl, —N-di-C$_{1-10}$-alkyl, OH or —O—C$_{1-10}$-alkyl, in conjunction with any of the above or below embodiments.

In another embodiment, the invention provides compounds of Formulas I or II wherein each R$^3$, independently, is H, C$_{1-10}$-alkyl, halo, CN, haloalkyl, NO$_2$, NH$_2$, —NH—C$_{1-10}$-alkyl, —N-di-C$_{1-10}$-alkyl, OH or —O—C$_{1-10}$-alkyl, the C$_{1-10}$-alkyl optionally comprising 1-3 heteroatoms selected from N, O and S and optionally substituted with one or more substituents of R$^5$ or R$^6$, in conjunction with any of the above or below embodiments.

In another embodiment, the invention provides compounds of Formulas I or II wherein each R$^3$, independently, is H, in conjunction with any of the above or below embodiments.

In another embodiment, the invention provides compounds of Formulas I or II wherein R$^4$ is C$_{1-10}$-alkyl, C$_{2-10}$-alkynyl or C$_{2-10}$-alkynyl, each of the C$_{1-10}$-alkyl, C$_{2-10}$-alkenyl and C$_{2-10}$-alkynyl optionally comprising 1-3 heteroatoms selected from N, O and S and optionally substituted with one or more substituents of R$^5$ or R$^6$, in conjunction with any of the above or below embodiments.

In another embodiment, the invention provides compounds of Formulas I or II wherein R$^4$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R$^5$, R$^6$, oxo, NR$^6$R$^6$, OR$^6$, SR$^6$, C(O)R$^6$, COOR$^6$, C(O)NR$^6$R$^6$, NR$^6$C(O)R$^6$, NR$^6$C(O)NR$^6$R$^6$, OC(O)NR$^6$R$^6$, S(O)$_2$R$^6$, S(O)$_2$NR$^6$R$^6$ or NR$^6$S(O)$_2$R$^6$, in conjunction with any of the above or below embodiments.

In another embodiment, the invention provide compounds of Formulas I or II wherein R⁴ is phenyl, naphthyl, pyridyl, pyrimidyl, pyridazinyl, pyrazinyl, triazinyl, quinolinyl, isoquinolinyl, quinazolinyl, isoquinazolinyl, aza-quinazolinyl, phthalazinyl, aza-phthalazinyl, thiophenyl, furyl, pyrrolyl, pyrazolyl, imidazolyl, triazolyl, thiazolyl, oxazolyl, isoxazolyl, isothiazolyl, indolyl, isoindolyl, indolinyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each ring of which is optionally substituted independently with one or more substituents of R⁵ or R⁶, in conjunction with any of the above or below embodiments.

In another embodiment, the invention provide compounds of Formulas I or II wherein R⁴ is phenyl, pyridyl, pyrimidyl, pyridazinyl, pyrazinyl, triazinyl, thiophenyl, furyl, pyrrolyl, pyrazolyl, imidazolyl, triazolyl, thiazolyl, oxazolyl, isoxazolyl, isothiazolyl, indolyl, isoindolyl, indolinyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each ring of which is optionally substituted independently with one or more substituents of R⁵ or R⁶, in conjunction with any of the above or below embodiments.

In another embodiment, the invention provide compounds of Formulas I or II wherein R⁴ is phenyl, pyridyl, pyrimidyl, pyridazinyl, pyrazinyl, triazinyl, thiophenyl, furyl, pyrrolyl, pyrazolyl, imidazolyl, triazolyl, thiazolyl, oxazolyl, isoxazolyl, isothiazolyl, indolyl, isoindolyl, indolinyl, tetrahydrofuranyl, pyrrolidinyl, oxazolinyl, isoxazolinyl, thiazolinyl or pyrazolinyl, each ring of which is optionally substituted independently with one or more substituents of R⁵ or R⁶, in conjunction with any of the above or below embodiments.

In another embodiment, the invention provide compounds of Formulas I or II wherein R⁴ is phenyl optionally substituted independently with one or more substituents of R⁵ or R⁶, in conjunction with any of the above or below embodiments.

In another embodiment, the invention provide compounds of Formulas I or II wherein each of B¹, B², B³ and B⁴, independently, is CR³;

D is an optionally substituted ring selected from

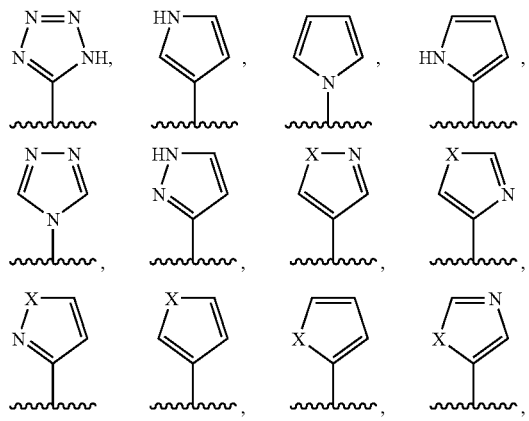

-continued

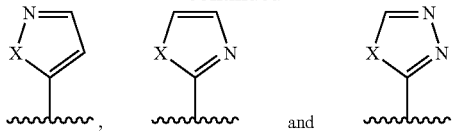

wherein X is NR⁶, O or S;

L¹ is NR³, O or S;

L² is —NR³—, —(CR³R³)$_n$C(O)NR³— or —(CR³R³)$_n$NR³C(O)—; and

R⁴ is phenyl, naphthyl, pyridyl, pyrimidyl, pyridazinyl, pyrazinyl, triazinyl, quinolinyl, isoquinolinyl, quinazolinyl, isoquinazolinyl, aza-quinazolinyl, phthalazinyl, aza-phthalazinyl, thiophenyl, furyl, pyrrolyl, pyrazolyl, imidazolyl, triazolyl, thiazolyl, oxazolyl, isoxazolyl, isothiazolyl, indolyl, isoindolyl, indolinyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each ring of which is optionally substituted independently with one or more substituents of R⁵ or R⁶, in conjunction with any of the above or below embodiments.

In other embodiments, Formulas I and II include the various of the exemplary compounds described in the experimentals methods section hereinbelow.

Definitions

The following definitions should assist in understanding the invention described herein.

The term "comprising" is meant to be open ended, including the indicated component(s), but not excluding other elements.

The term "$C_{\alpha-\beta}$ alkyl", when used either alone or within other terms such as "haloalkyl" and "alkylamino", embraces linear or branched radicals having α to β number of carbon atoms (such as $C_1$-$C_{10}$). Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals.

Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two (heterobicyclic) or even three (heterotricyclic) rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S', as used herein, means that the ring or ring system may be a carbocycle, an aryl, a heterocycle or a heteroaryl monocyclic, bicyclic or tricyclic ring or ring system.

The term "alkylamino" includes "N-alkylamino" where amino radicals are independently substituted with one alkyl radical. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Examples of such lower alkylamino radicals include N,N-dimethylamino, N,N-diethylamino, and the like.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "Formula I" includes any sub formulas. Similarly, the term "Formula II" includes any sub formulas.

The term "pharmaceutically-acceptable" when used with reference to a compound of Formulas I or II is intended to refer to a form of the compound that is safe for administration. For example, a salt form, a solvate, a hydrate or derivative form of a compound of Formula I or of Formula II, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I and II are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I and II may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I or II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I. A "pharmaceutically-acceptable prodrug" as used herein, denotes a prodrug which is pharmaceutically acceptable. Pharmaceutically acceptable modifications to the compounds of Formula I are readily appreciated by those of ordinary skill in the art.

The compound(s) of Formula I or II may be used to treat a subject by administering the compound(s) as a pharmaceutical composition, also referred to herein as a medicament. To this end, the compound(s) can be combined with one or more excipients, including carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The term "angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction and/or flow properties to improve blood perfusion of tissue.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Tie-2, and similar kinases, in the mammal.

General Synthetic Procedures

The present invention further comprises procedures for the preparation of a compound of Formulas I and II. The compounds of Formulas I and II can be synthesized according to the procedures described in the following Schemes 1-5, wherein the substituents are as defined for Formulas I and II, above, except where further noted. The synthetic methods described below are merely exemplary, and the compounds of the invention may be synthesized by alternate routes as appreciated by persons of ordinary skill in the art. The compounds exemplified herein are named using either the IUPAC naming convention or the naming convention of MDL or ChemDraw software.

The following list of abbreviations used throughout the specification represent the following and should assist in understanding the invention:

ACN, MeCN—acetonitrile
BSA—bovine serum albumin
$Cs_2CO_3$—cesium carbonate
$CHCl_3$—chloroform
$CH_2Cl_2$, DCM—dichloromethane, methylene chloride
DIC—1,3-diisopropylcarbodiimide
DIEA,$(ipr)_2$NEt—diisopropylethylamine
DME—dimethoxyethane
DMF—dimethylformamide
DMAP—4-dimethylaminopyridine
DMSO—dimethylsulfoxide
EDC—1-(3-dimethylaminopropyl)-3-ethylcarbodiimide
Et2O—diethyl ether
EtOAc—ethyl acetate
PyBop—benzotriazol-1-yl-oxy-tripyrrolidino-phosphonium hexafluorophosphate
RT, rt—room temperature
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran
G, gm—gram
h, hr—hour
$H_2$—hydrogen
HATU—O-(7-azabenzotriazol-1-yl)-N,N,N',N'-tetramethyluroniumhexafluorophosphate
HOBt—1-hydroxybenzotriazole hydrate
HPLC—high pressure liquid chromatography
IPA, IpOH—isopropyl alcohol
$K_2CO_3$—potassium carbonate
$MgSO_4$—magnesium sulfate
MeOH—methanol
$N_2$—nitrogen
$NaHCO_3$—sodium bicarbonate
$NaOCH_3$—sodium methoxide
$Na_2SO_4$—sodium sulfate
$NH_4Cl$—ammonium chloride
$NH_4OH$—ammonium hydroxide
Pd/C—palladium on carbon Scheme 1

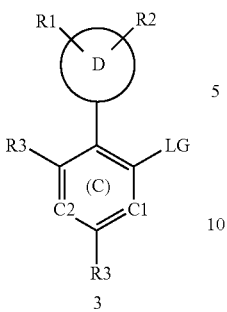

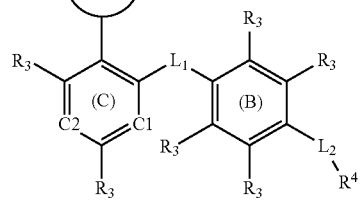

The biaryl ring system (3), including substituted or unsubstituted 5-membered heteroaryl coupled-pyridines or pyrimidines (both $C^1$ and $C^2$=N) and generally referred to herein as the C-D ring portion of the compounds of Formulas I-III, can be prepared according to the method generally described in Scheme 1. As shown, Suzuki coupling methodology utilizing an heteroaryl halide (1) where X is a halide such as iodide, bromide or chloride, and an aryl borinate (2) in the presence of palladium, such as $Pd(PPh_3)_4$, and a weak base, such as a $Na_2CO_3$, $K_2CO_3$ or $NaHCO_3$ in a polar solvent such as DME can be used to synthesize compound (3). LG is a leaving group, such as F or Cl. Similarly, other known aryl coupling methods, such as use of stannanes, zincates and copper coupling techniques are also suitable to prepare compound (3).

As shown in Scheme 2, compounds (18 and 18a) comprising biaryl amines, ethers and thiols (where $L^1$=NH, O and S, respectively) can be prepared by reacting compound (16) (where LG is a leaving group, such as a halide) with a nucleophilic phenyl compounds (17 and 17a) wherein G is a suitable nucleophile, such as NHR or $NH_2$ (Scheme 6), OH, SH or carbon nucleophile, sufficient to displace the chloride from ring C of compound (16). For example, phenols (G=O) and thiols (G=S) can be coupled with activated aryl chlorides to form the biaryl ethers and thiols (compounds 18 and 18a) using weak bases such as TEA, or inorganic bases such as $Cs_2CO_3$, in DMSO at elevated temperatures, such as ranging form about 70° C. to about 130° C.

Anilines (compounds 17 and 17a) can be coupled with activated aryl chlorides (compound 16) to form biaryl anilines (compounds 18 and 18a) using Pd catalysis or $NEt_3 \cdot TFA$ under suitable conditions, which may or may not require the input of heat.

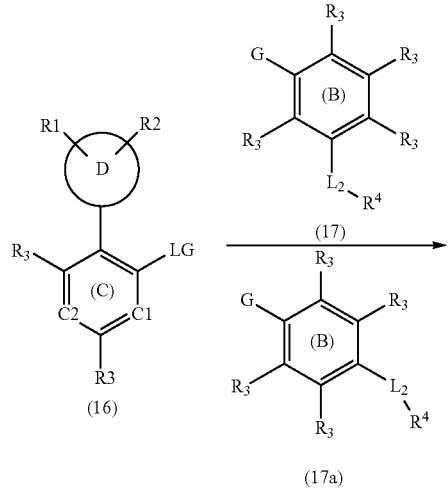

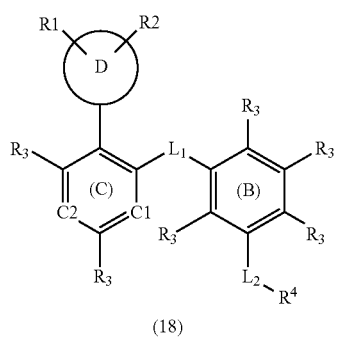

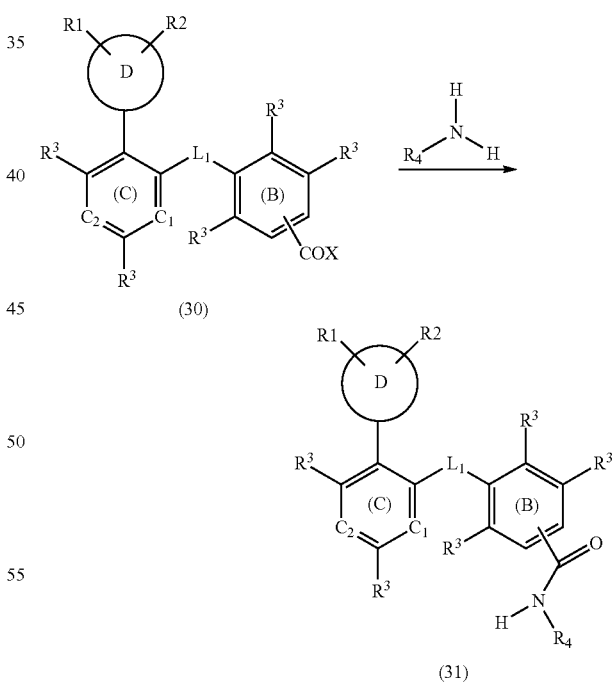

As shown, amides can be prepared according to the method illustrated in Scheme 3. Substituted primary and secondary amines can be coupled with a free acid of ring B using a suitable coupling reagent, such as EDC, TBTU, HBTU, HOBT, DCC, HATU and others known in the art, via the corresponding acid-chloride or other acid halide. The acid-halide in compound (30) is designated as C(O)—X, where X is a suitable halide such as a chloride or fluoride. An acid chloride can be formed by reacting the free acid with oxalyl chloride, POCl₃ or similar reagent in a suitable solvent. Te amide bond may also be effected using other known, conventional acid activated leaving groups. Such reactions generally proceed well in an inert, non-nucleophilic solvent(s), such as DMF, DMSO, CH₂CL₂ and the like, at ambient temperatures. Poor solubility of the coupling reagent and/or the intermediates may generally require use of polar solvents. In some cases, depending upon the particular substrate or intermediates (30) and/or the amine starting material, heat may be necessary to effect the transformation and/or a higher yield. While Scheme 10 illustrates compound (31) having the amide corresponding to $R^7$ or $R^8$, the invention is not so limited and such method is applicable to ring B having a free acid at any of positions $R^3$, respectively.

Scheme 4

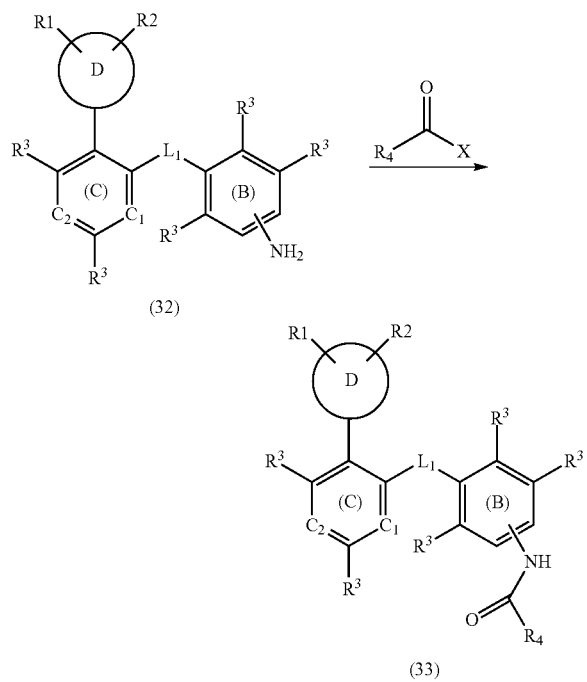

(32)

(33)

As shown, reverse amides can be prepared according to the method illustrated in Scheme 4. Substituted free carboxylic acids may be coupled with the amine of compound (32) utilizing common coupling reagents and methods, such as those described in Scheme 3, to form the corresponding amide. Heat may be used where necessary. As in Scheme 3, Scheme 4 is not limited to compounds wherein the amide corresponds to a meta position, but may also be in the para position relative ring B as in Formulas II.

Scheme 5

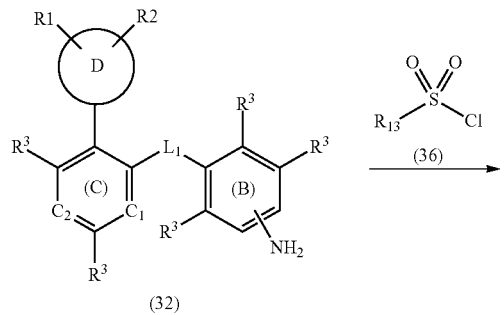

(32)

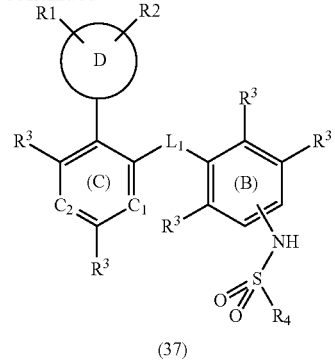

(37)

As shown, sulfonamides (37) can be prepared according to the method illustrated in Scheme 5. Anilines (32) are coupled with substituted sulfonyl chlorides (36) in the presence of a weak base, such as a tertiary amine or pyridine, in inert, non-nucleophilic, anhydrous solvents, such as DMF, CHCL₃ CH₂Cl₂, toluene and the like, at mild conditions, such as at room temperature, to form the desired sulfonamide (37). In some cases, depending upon the particular intermediates (32) and/or (36), their concentration in the solvent medium and independent reactivity, heat may be necessary to effect the transformation and/or a higher yield.

To enhance the understanding of the invention described herein, the following examples are set forth. It should be appreciated that these examples are merely for illustrative purposes only and are not to be construed as limiting the scope of this invention in any manner.

Analytical Methods:

Unless otherwise indicated, the reactions were monitored by TLC. Merck (silica gel Si-60 F₂₅₄, 0.25 mm) and purified by Flash chromatography using Merck silica gel Si-60 (230-400 mesh).

LC-MS Method:

The final product compounds were analyzed using analytical HPLC: column (Develosil RPAq 4.6×50 mm), flow: 1.5 ml/min; UV detection at 220 nm and 254 nm; with one of the following solvent gradients:

A: 5% MeCN, 95% H2O (0.1% TFA) to 100% MeCN in 5 min
B: 10% MeCN, 90% H2O (0.1% TFA) to 100% MeCN in 5 min
C: 20% MeCN, 80% H₂O (0.1% TFA) to 100% MeCN in 5 min
D: 30% MeCN, 70% H2O (0.1% TFA) to 100% MeCN in 5 min
E: 40% MeCN, 60% H2O (0.1% TFA) to 100% MeCN in 5 min
F: 50% MeCN, 50% H2O (0.1% TFA) to 100% MeCN in 5 min
G: 10% MeCN, 90% H2O (0.1% TFA) to 30% MeCN, 70% H₂O (0.1% TFA) in 5 min
H: 10% MeCN, 90% H2O (0.1% TFA) to 40% MeCN, 60% H₂O (0.1% TFA) in 5 min Preparative HPLC Method:

Where indicated, compounds of interest were purified via preparative HPLC: VP100/21 Nucleosil 50-100 (Macherey-Nagel), eluting with hexane/EtOAc/MeOH or CH₂Cl2/MeOH/NH3-MeOH gradients.

Proton NMR Spectra:

Unless otherwise indicated, all ¹H NMR spectra were run on a Bruker, ¹H-NMR (300 MHz), ³C-NMR (75 MHz) in the indicated deuterated solvent at ambient temperature. The chemical shifts (S) are expressed in ppm, and the coupling constants J are reported in Hz.

Mass Spectra (MS)

Unless otherwise indicated, all mass spectral data for starting materials, intermediates and/or exemplary compounds were run on a Finnagan uinstrument and are reported as mass/charge (m/z), having an (M+H$^+$) molecular ion. The molecular ion reported was obtained by atmospheric pressure chemical ionization (APCI) method. Compounds having an isotopic atom, such as bromine and the like, are reported according to the detected isotopic pattern, as appreciated by those skilled in the art.

EXAMPLE 1

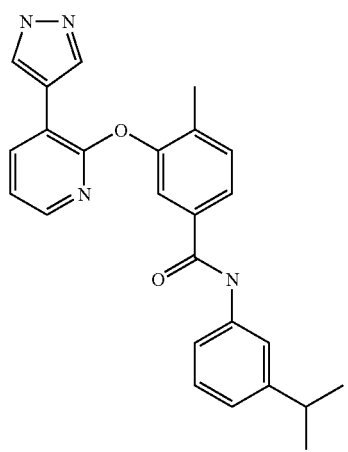

Synthesis of 3-(3-(1H-pyrazol-4-yl)pyridin-2-yloxy)-N-(3-isopropylphenyl)-4-methylbenzamide Step 1: 1-Benzyl-4-iodo-1H-pyrazole (1.35 g, 4.77 mmol), 2-chloropyridin-3-ylboronic acid (1.50 g, 9.53 mmol), sodium bicarbonate (1.20 g, 14.3 mmol) and Pd(PPh$_3$)$_4$ (276 mg, 0.239 mmol) were combined in an argon-purged sealed tube. Dimethoxyethane (8 mL) and water (5 mL) were added and the mixture was heated to 85° C. for 16 hours. The reaction was cooled to rt, diluted with water and extracted into EtOAc. The separated organic layer was dried over anhydrous sodium sulfate, filtered and concentrated. This residue was purified by silica gel chromatography (50-75% EtOAc/hexanes) to yield 3-(1-benzyl-1H-pyrazol-4-yl)-2-chloropyridine as a light yellow oil after concentration. MS m/z=270 [M+1]$^+$. Calc'd for C$_{15}$H$_{12}$FN$_3$: 269.74.

Step 2: 3-Hydroxy-4-methylbenzoic acid (1.07 g, 7.00 mmol), 3-isopropylbenzenamine (0.90 mL, 6.4 mmol), and DMAP (0.27 g, 2.2 mmol) were suspended in 25 mL dry toluene in a 2-neck flask with an attached Dean-Stark trap under N$_2$. The mixture was stirred in a 135° C. oil bath and brought to a boil before PCl$_3$ (0.28 mL, 3.2 mmol) was added dropwise by glass/Teflon syringe over 15 minutes. Heating was continued an additional 25 minutes. After cooling, the mixture was diluted with brine and ethyl acetate, and acidified with 1 NHC1. After extraction, the organic layer was dried over anhydrous Na$_2$SO$_4$, concentrated, and purified by flash chromatography (20-50% EtOAc/hexanes) to yield 3-hydroxy-N-(3-isopropylphenyl)-4-methylbenzamide as a white solid after concentration. MS m/z=268 [M−1]$^−$. Calc'd for C$_{17}$H$_{19}$NO$_2$: 269.35.

Step 3: 3-Hydroxy-N-(3-isopropylphenyl)-4-methylbenzamide (100 mg, 0.371 mmol), cesium carbonate (220 mg, 0.676 mmol) and 3-(1-benzyl-1H-pyrazol-4-yl)-2-chloropyridine (91.0 mg, 0.338 mmol) were combined in an argon-purged sealed tube. DMSO (1.5 mL) was added and the mixture was heated to 130° C. for 23 hours. The cooled reaction was diluted with EtOAc and water and then neutralized with TFA (pH~7). The separated organic layer was dried over anhydrous sodium sulfate, filtered and concentrated. The residue was purified first by silica gel chromatography (1:1 MTBE/benzene) followed by trituration of the resulting solid with 20:1 hexanes/EtOAc to yield 3-(3-(1-benzyl-1H-pyrazol-4-yl)pyridin-2-yloxy)-N-(3-isopropylphenyl)-4-methylbenzamide as an off-white solid. MS m/z=503 [M+1]$^+$. Calc'd for C$_{32}$H$_{30}$N$_4$O$_2$: 502.62.

Step 4: To 3-(3-(1-benzyl-1H-pyrazol-4-yl)pyridin-2-yloxy)-N-(3-isopropylphenyl)-4-methylbenzamide (65 mg, 0.13 mmol) in EtOAc (4 mL) and MeOH (4 mL) was added Pd/C (10%, 300 mg). The reaction was purged with hydrogen gas and then stirred at rt under a balloon of hydrogen for 16 hours. The reaction was filtered through Celite with EtOAc, concentrated, and purified by Gilson reverse-phase HPLC (0.1% TFA in water/acetonitrile). After a basic workup involving CH$_2$Cl$_2$ and saturated sodium bicarbonate, 3-(3-(1H-pyrazol-4-yl)pyridin-2-yloxy)-N-(3-isopropylphenyl)-4-methylbenzamide was obtained as a white solid. MS m/z=413 [M+1]$^+$. Calc'd for C$_{25}$H$_{24}$N$_4$O$_2$: 412.50.

EXAMPLE 2

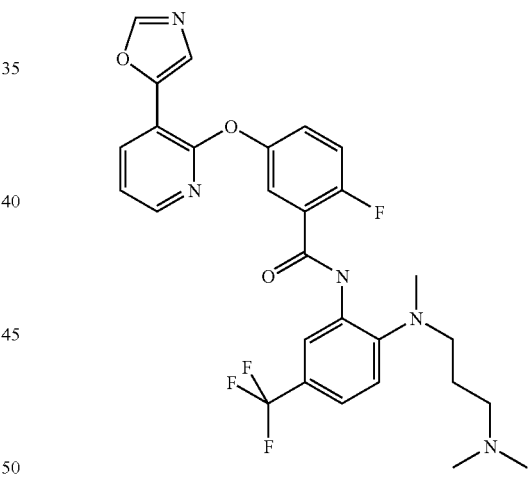

Synthesis of N-(2-((3-(dimethylamino)propyl)(methyl)amino)-5-(trifluoromethyl)phenyl)-2-fluoro-5-(3-(oxazol-5-yl)pyridin-2-yloxy)benzamide Step 1: To 2-chloronicotinaldehyde (381 mg, 2.69 mmol), 2-fluoro-5-hydroxybenzoic acid (300 mg, 1.92 mmol) and cesium carbonate (1.25 g, 3.84 mmol) was added DMSO (2.5 mL). The mixture was heated to 80° C. in a sealed tube for 3 hours. The cooled reaction was diluted with water and extracted with EtOAc. The aqueous layer was acidified with TFA (pH~3) and extracted with EtOAc. This layer was dried over anhydrous sodium sulfate, filtered and concentrated. The residue was washed with Et$_2$O dried to yield 2-fluoro-5-(3-formylpyridin-2-yloxy)benzoic acid as an off-white solid. MS m/z=262 [M+1]$^+$. Calc'd for C$_{13}$H$_8$FNO$_4$: 261.21.

Step 2: To 2-fluoro-5-(3-formylpyridin-2-yloxy)benzoic acid (230 mg, 0.881 mmol) and TosMIC (172 mg, 0.881 mmol) in DME (8.0 mL) was added DBU (0.29 mL, 1.9 mmol). The mixture was heated to 85° C. for 2.5 hours in a sealed tube. After concentrated, the residue was diluted with saturated sodium carbonate and extracted with EtOAc. The aqueous layer was acidified with TFA (pH~3) and the resulting solid was filtered and dried to yield 2-fluoro-5-(3-(oxazol-5-yl)pyridin-2-yloxy)benzoic acid as a beige solid. MS m/z=301 [M+1]$^+$. Calc'd for $C_{15}H_9FN_2O_4$: 300.25.

Step 3: To 2-fluoro-5-(3-(oxazol-5-yl)pyridin-2-yloxy) benzoic acid (196 mg, 0.653 mmol) in $CH_2Cl_2$ (6.0 mL) was added oxalyl chloride (0.28 mL, 3.3 mmol) followed by DMF (2 drops). The mixture was stirred under nitrogen at rt for 15 hours. The reaction was concentrated to yield 2-fluoro-5-(3-(oxazol-5-yl)pyridin-2-yloxy)benzoyl chloride, which was used without further purification.

Step 4: To 2-fluoro-5-(3-(oxazol-5-yl)pyridin-2-yloxy) benzoyl chloride (60 mg, 0.17 mmol) and $N^1$-(3-(dimethylamino)propyl)-$N^1$-methyl-4-(trifluoromethyl)benzene-1,2-diamine (44.1 mg, 0.160 mmol) was added THF (1.0 mL). The mixture was stirred at rt for 4.5 days. The reaction was quenced with excess triethylamine, filtered and concentrated. The residue was purified by Gilson reverse-phase HPLC (0.1% TFA in water/acetonitrile). After basic workup, N-(2-((3-(dimethylamino)propyl)(methyl)amino)-5-(trifluoromethyl)phenyl)-2-fluoro-5-(3-(oxazol-5-yl)pyridin-2-yloxy) benzamide was obtained as a white solid. MS m/z=558 [M+1]$^+$. Calc'd for $C_{28}H_{27}F_4N_5O_3$: 557.55.

EXAMPLE 3

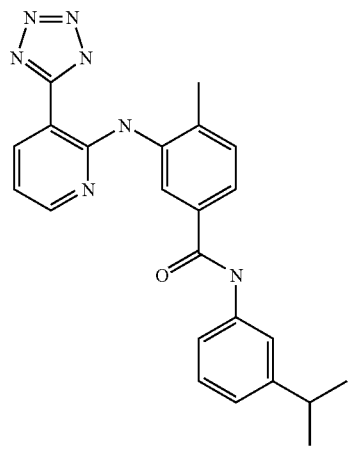

Synthesis of 3-(3-(1H-tetrazol-5-yl)pyridin-2-ylamino)-N-(3-isopropylphenyl)-4-methylbenzamide Step 1: To 2-chloronicotinonitrile (140 mg, 1.00 mmol) and 3-amino-N-(3-isopropyl-phenyl)-4-methyl-benzamide (80 mg, 0.30 mmol) was added isopropanol (0.8 mL) and TFA (12 drops). The mixture was heated to 130° C. for 16 hours in a sealed tube. The cooled mixture was purified by silica gel chromatography (25% EtOAc/hexanes) to yield 3-(3-cyanopyridin-2-ylamino)-N-(3-isopropylphenyl)-4-methylbenzamide. MS m/z [M+H]$^+$=371; Calc'd for $C_{23}H_{22}N_4O$: 370.46.

Step 2: To 3-(3-cyanopyridin-2-ylamino)-N-(3-isopropylphenyl)-4-methylbenzamide (11 mg, 0.03 mmol), sodium azide (21 mg, 0.30 mmol) and ammonium chloride (17 mg, 0.30 mmol) was added DMF (0.5 mL). The mixture was heated to 130° C. in the microwave for 10 minutes. The reaction was quenched with saturated sodium bicarbonate and extracted with EtOAc. The organic layer was dried over anhydrous sodium sulfate, filtered and concentrated to yield 3-(3-(1H-tetrazol-5-yl)pyridin-2-ylamino)-N-(3-isopropylphenyl)-4-methylbenzamide. MS m/z [M+H]$^+$=414; Calc'd for $C_{23}H_{23}N_7O$: 413.49.

EXAMPLE 4

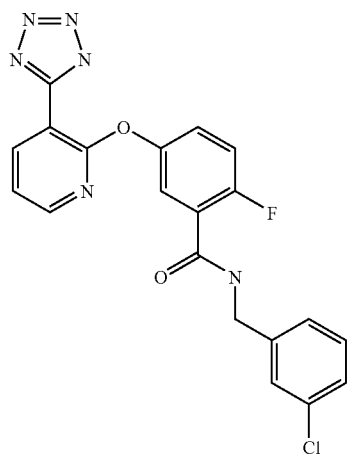

Synthesis of 5-(3-(1H-tetrazol-5-yl)pyridin-2-yloxy)-N-(3-chlorobenzyl)-2-fluorobenzamide Step 1: To 2-chloronicotinonitrile (900 mg, 6.50 mmol), 2-fluoro-5-hydroxybenzoic acid (1.0 g, 6.4 mmol) and cesium carbonate (4.2 g, 13 mmol) was added DMSO (7 mL). The mixture was heated to 95° C. for 18 hours in a sealed tube. The mixture was diluted with water and extracted with EtOAc. The aqueous layer was acidified with 6 N HCl (pH~2) and then extracted with EtOAc. The organic layer was dried over anhydrous sodium sulfate, filtered and concentrated to yield 5-(3-cyanopyridin-2-yloxy)-2-fluorobenzoic acid. MS m/z 257=[M+H]$^+$. Calc'd for $C_{13}H_7FN_2O_3$: 258.21.

Step 2: To 5-(3-cyanopyridin-2-yloxy)-2-fluorobenzoic acid (1.2 g, 4.6 mmol) in $CH_2Cl_2$ (5 mL) was added oxalyl chloride (0.43 mL, 5.0 mmol) followed by 5 drops of DMF at 0° C. The mixture was stirred at rt for 16 hours. The mixture was concentrated and the resulting 5-(3-cyanopyridin-2-yloxy)-2-fluorobenzoyl chloride was used without purification.

Step 3: To 5-(3-cyanopyridin-2-yloxy)-2-fluorobenzoyl chloride (100 mg, 0.362 mmol) in THF (1 mL) was added (3-chlorophenyl)methanamine (52 mg, 0.36 mmol). The mixture was stirred at rt for 16 hours. After concentration, the residue was purified by Gilson reverse-phase HPLC (0.1% TFA in water/acetonitrile). A basic workup with $CH_2Cl_2$ and saturated sodium bicarbonate yielded N-(3-chlorobenzyl)-5-(3-cyanopyridin-2-yloxy)-2-fluorobenzamide. MS m/z 382= [M+H]$^+$. Calc'd for $C_{20}H_{13}ClFN_3O_2$: 381.80.

Step 4: Analogous to procedure from Step 2 of 3-(3-(1H-tetrazol-5-yl)pyridin-2-ylamino)-N-(3-isopropylphenyl)-4-methylbenzamide synthesis. Yielded 5-(3-(1H-tetrazol-5-yl)

pyridin-2-yloxy)-N-(3-chlorobenzyl)-2-fluorobenzamide. MS m/z 425=[M+H]$^+$. Calc'd for $C_{20}H_{14}ClFN_6O_2$: 424.82.

EXAMPLE 5

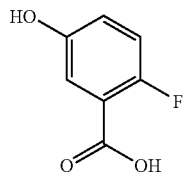

Synthesis of 2-Fluoro-5-hydroxybenzoic acid

To 2-fluoro-5-methoxybenzoic acid (5.00 g, 29.4 mmol) was added 49% aqueous HBr (50 mL) and glacial acetic acid (40 mL). The mixture was heated overnight at 140° C., cooled to RT, diluted with ice water and extracted with EtOAc. The organic layer was dried over $Na_2SO_4$, filtered and concentrated to yield 2-fluoro-5-hydroxybenzoic acid. MS m/z=157 [M+1]$^+$. Calc'd for $C_7H_5FO_3$: 156.11.

EXAMPLE 6

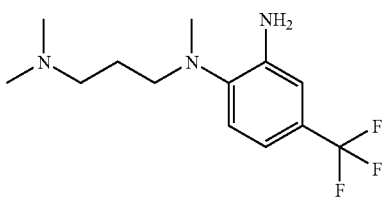

Synthesis of $N^1$-(3-(dimethylamino)propyl)-$N^1$-methyl-4-(trifluoromethyl)benzene-1,2-diamine Step 1: The title compound was made using a procedure described in Collins, et. al., *Tetrahedron, Vol.* 48, No. 37, pp 7887-7898, 1992. To a solution of 1-fluoro-2-nitro-4-trifluoromethyl-benzene (1.0 g, 4.78 mmol) in dry THF (24 mL) was added $N^1,N^1,N^3$-trimethylpropane-1,3-diamine (0.64 mL, 5.7 mmol). The solution turned bright yellow. NaHCO$_3$ (1.1 g, 13 mmol) was added and the reaction was stirred at room temperature and monitored by LCMS. The reaction was filtered and concentrated before being taken up in CH$_2$Cl$_2$ and H$_2$O. The organic layer was separated, dried with MgSO$_4$, filtered, and concentrated to afford the title compound as an orange-brown oil.

Step 2: To N-(3-(dimethylamino)propyl)-N-methyl-2-nitro-4-(trifluoromethyl)benzenamine (1.46 g, 5.05 mmol) in dry MeOH (50 mL) was added Pd/C (10%, 535 mg). H$_2$ gas was bubbled through the solution at room temperature overnight with vigorous stirring. The reaction mixture was filtered through celite to provide, after concentration, the title compound as an orange solid. MS m/z (M+H)$^+$=276; Calc'd for $C_{13}H_{20}F_3N_3$: 275.32.

EXAMPLE 7

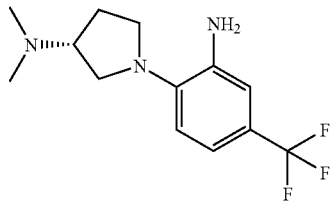

(R)-1-(2-amino-4-(trifluoromethyl)phenyl)-N,N-dimethylpyrrolidin-3-amine

MS m/z=274 [M+H]$^+$. Calc'd for $C_{13}H_{18}F_3N_3$: 273.30.

EXAMPLE 8

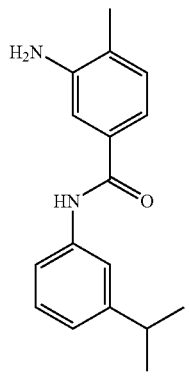

Synthesis of 3-amino-N-(3-isopropyl-phenyl)-4-methyl-benzamide

Step 1: To a solution of 4-methyl-3-nitro-benzoyl chloride (2.00 g, 0.010 mol) in THF (30 mL), in a water bath-cooled 100 mL RBF, was added 3-isopropyl-phenylamine (1.35 g, 0.010 mol) dropwise. The reaction was allowed to stir at room temperature for 1 hour before being concentrated. The mixture was taken up in EtOAc and washed with NaHCO$_3$ (aq., conc.) and then brine. The solution was dried over MgSO$_4$, filtered, and concentrated to yield N-(3-isopropyl-phenyl)-4-methyl-3-nitro-benzamide as an orange oil that solidifies upon standing. MS m/z 299=[M+H]$^+$. Calc'd for $C_{17}H_{18}N_2O_3$: 298.34.

Step 2: To N-(3-isopropyl-phenyl)-4-methyl-3-nitro-benzamide (3.0 g, 0.010 mol) dissolved in EtOAc (60 mL) in a 100 mL RBF was added Pd/C (10%, 250 mg). The flask was capped with a rubber septum and flushed with H$_2$ gas through a balloon/needle. Positive H$_2$ pressure was applied through the balloon/needle and reaction was stirred vigorously at room temperature for 3 days. TLC indicated clean conversion of starting material. The reaction was filtered through a pad of sand/celite. After concentration, the mixture was purified by silica gel chromatography to afford a light orange oil. Trituration with a mixture of hexanes and EtOAc afforded 3-amino-N-(3-isopropyl-phenyl)-4-methyl-benzamide as an off-white solid. MS m/z 269=[M+H]$^+$. Calc'd for $C_{17}H_{20}N_2O$: 268.36.

The following Exemplary compounds were synthesized using a method analogous to one or more of those described in Examples 1-4.

| Ex. No. | Compound Name | MS Data [M + 1]+ | Method |
|---|---|---|---|
| 9 | 3-(3-(1H-tetrazol-5-yl)pyridin-2-yloxy)-N-(3-isopropylphenyl)-4-methylbenzamide | 415 | 4 |
| 10 | 3-(3-(1-benzyl-1H-pyrazol-4-yl)pyridin-2-yloxy)-N-(3,isopropylphenyl)-4-methylbenzamide | 504 | 1 |
| 11 | 3-(3-(1H-pyrazol-4-yl)pyridin-2-yloxy)-N-(5-cyclohexyl-2-methoxyphenyl)-4-methylbenzamide | 484 | 1 |
| 12 | 3-(3-(1H-tetrazol-5-yl)pyridin-2-ylamino)-N-(3-isopropylphenyl)-4-methylbenzamide | 414 | 3 |
| 13 | 3-(3-(2H-tetrazol-5-yl)pyridin-2-ylamino)-N-(3-isopropylphenyl)benzamide | 400 | 3 |
| 14 | N-(3-isopropylphenyl)-4-methyl-3-(3-(oxazol-5-yl)pyridin-2-yloxy)benzamide | 414 | 2 |
| 15 | 3-(3-(1H-pyrazol-5-yl)pyridin-2-yloxy)-4-methyl-N-(3-(trifluoromethyl)phenyl)benzamide | 439 | 4 |
| 16 | 2-fluoro-5-(3-(oxazol-5-yl)pyridin-2-yloxy)-N-(3-(trifluoromethoxy)phenyl)benzamide | 460 | 2 |
| 17 | 2-fluoro-N-(3-methoxy-5-(trifluoromethyl)phenyl)-5-(3-(oxazol-5-yl)pyridin-2-yloxy)benzamide | 474 | 2 |
| 18 | N-(3-isopropylphenyl)-4-methyl-3-(2-(oxazol-5-yl)phenoxy)benzamide | 413 | 2 |
| 19 | N-(2-((3-(dimethylamino)propyl)(methyl)amino)-5-(trifluoromethyl)phenyl)-4-methyl-3-(2-(oxazol-5-yl)phenoxy)benzamide | 554 | 2 |
| 20 | N-(2-((3-(dimethylamino)propyl)(methyl)amino)-5-(trifluoromethyl)phenyl)-4-methyl-3-(3-(oxazol-5-yl)pyridin-2-yloxy)benzamide | 555 | 2 |
| 21 | N-(2-((R)-3-(dimethylamino)pyrrolidin-1-yl)-5-(trifluoromethyl)phenyl)-4-methyl-3-(3-(oxazol-5-yl)pyridin-2-yloxy)benzamide | 553 | 2 |
| 22 | 4-methyl-3-(3-(oxazol-5-yl)pyridin-2-yloxy)-N-(3-(trifluoromethyl)phenyl)benzamide | 440 | 2 |
| 23 | N-(4-(3-(1H-pyrazol-4-yl)pyridin-2-yloxy)phenyl)-2-(phenylamino)benzamide | 448 | 1 |
| 24 | N-(4-(3-(1H-pyrazol-4-yl)pyridin-2-yloxy)phenyl)-3-(trifluoromethyl)benzamide | 425 | 1 |
| 25 | N-(4-(3-(3-amino-1H-pyrazol-4-yl)pyridin-2-yloxy)phenyl)-2-(phenylamino)benzamide | 464 | 1 |
| 26 | N-(4-(3-(oxazol-5-yl)pyridin-2-yloxy)phenyl)-2-(phenylamino)benzamide | 449 | 2 |

While the examples described above provide processes for synthesizing compounds of Formulas I and II, other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jeschert, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$;

acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of these compounds are expressly included in the present invention.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

Alternatively, a compound of any of the formulas described herein may be synthesized according to any of the procedures described herein. In the procedures described herein, the steps may be performed in an alternate order and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

These detailed descriptions fall within the scope, and serve to exemplify, the above-described General Synthetic Procedures which form part of the invention. These detailed descriptions are presented for illustrative purposes only and are not intended as a restriction on the scope of the invention.

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I and II) vary with structural change, in general, activity possessed by compounds of Formulas I and II may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to inhibit the activity of various kinase enzymes, including, without limitation, Tie-2 and Aurora receptor kinases at doses less than 25 μM.

Biological Evaluation

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of at least <25 μM in any one of the described assays, thereby demonstrating and confirming the utility of the compounds of the invention as protein kinase inhibitors and in the prophylaxis and treatment of immune diseases, proliferative disorders, angiogenic diseases, etc.

Tie-2—Homogenous Time Resolved Fluorescent (HTRF) Kinase Assay $IC_{50}$'s for the inhibition of the Tie-2 kinase enzyme for individual compounds were measured using an HTRF assay, utilizing the following procedure:

In a 96 well plate (available from Costar Co.) was placed 1 uL of each test and standard compound per well in 100% DMSO having a 25 uM final compound concentration (3-fold, 10 point dilution). To each well was added 20 uL of a reaction mix formed from Tie-2 (4.0 uL; of a 10 mM stock solution available from Gibco), 0.05% BSA (0.1 uL; from a 10% stock solution available from Sigma-Aldrich Co.), 0.002 mM of BLC HER-2 KKK (Biotinylated Long chain peptide; 0.04 uL; from a 0.002 mM stock solution), 0.01 mM concentration of ATP (0.02 uL; commercially available from Sigma-Aldrich Co.) and the remaining solution was water (15.84 uL) to make to a total volume of 20 uL/well.

The reaction was initiated in each well by adding 20 uL per well of an enzyme preparation consisting of a 50 mM concentration of Hepes (1.0 uL; from a 1000 mM stock solution commercially available from Gibco Co.), 0.05% concentration of BSA (0.1 uL), 4 mM of DTT (0.08 uL; from a 1000 mM stock solution available from Sigma-Aldrich Co.), a $2.4 \times 10^{-7}$ concentration of Tie-2 (0.02 uL, from a 4 mM concentration stock), with the remaining volume being water (18.8 uL) to dilute the enzyme preparation to a total volume of 20 uL. The plate was incubated for about 90 minutes at RT. After incubation, a 160 uL of a filtered detection mixture, prepared from 0.001 mg/ml of SA-APC (0.0765 uL; available as a 2.09 mg/ml stock solution from Gibco), 0.03125 nM concentration of Eu-Ab (0.1597 uL; available in a 31.3 nM stock solution from Gibco), with the remaining volume being Detection buffer (159.73 uL), was added to each well to stop the reaction therein. The plate was then allowed to equilibrate for about 3 hr and read on a Ruby Star fluorescent reader (available from BMG Technologies, Inc.) using a 4 parameter fit using activity base to calculate the corresponding $IC_{50}$'s for the test and standard compounds in each well. The following exemplary compounds were found to have $IC_{50}$'s for the inhibition of Tie-2 as measured by the HTRF assay of less than or equal to 5 uM: Examples 1-3 and 10-25. The following exemplary compounds were found to have $IC_{50}$'s for the inhibition of Tie-2 as measured by the HTRF assay of less than or equal to 1 uM: Examples 1-3 and 10-12, 14-16, 18-20 and 22-23.

The following exemplary compounds were found to have $IC_{50}$'s for the inhibition of Tie-2 as measured by the HTRF assay of less than or equal to 500 nM: Examples 1-2 and 10-12, 14-15, 18-20 and 22. The following exemplary compounds were found to have $IC_{50}$'s for the inhibition of Tie-2 as measured by the HTRF assay of less than or equal to 100 nM: Examples 1, 11, 14, 18 and 22.

Tie-2 Cell-Based Delfia Assay

Day 1—Plate Preparation

Three 175 ml flasks of EAHY926 cells were obtained from the University of N. Carolina. All cells were trypsinized (i.e., washed with 20 mL of PBS followed by 3 mL of trypsin-EDTA obtained from Gibco Co., cat. no. 25300-054, for 5 min at RT), then cultured in a growth medium solution containing DMEM (High glucose, Gibco Co., cat. no. 1965-092), 10% FBS serum (Gibco Co., cat. no. 10099-141) and P/S (Penicillin-Streptomycin-Glutamine; Gibco Co., cat. no. 10378-016) culture media. The cells were counted using a Z2® Coulter® counter. The cells were plated in four 24-well tissue culture plates (Costar Co., cat. no. 353047) to initially contain $4 \times 10^5$ cells/ml per well, and then loaded to 500 uL volume having a final cell density of $2 \times 10^5$ cells/well. The cells were incubated for 5 or more hours at 37° C. under 5% $CO_2$. The DMEM+10% serum+P/S culture media was removed and the cells washed twice with 500 uL of PBS (without Ca+ and Mg++; Gibco Co., cat. no. 14190-136) at RT. 500 uL of 0.5% FBS+F12 (F12 nutrient mixture; Gibco Co., cat. no. 11765-054) was added to each well and the cells were incubated at 37° C. overnight (about 15 hr).

100 ug of anti-hTie2 antibody (R & D Systems, Inc., Cat. No. AF313) was diluted with 10 mL of ice-cold PBS to prepare a 10 ug/mL antibody concentration stock. A 96-well microplate (Perkin-Elmer Wallac, cat. no. AAAND-0001) was coated with 100 uL of the anti-Tie2 antibody stock and the coated plate was stored at 4° C. overnight.

Day 2—Compound Plate Preparation

The media in the microplate was replaced with a preparation of 500 uL DMEM+1% BSA (Bovine Serum Albumin; ICN Biomedicals, Inc., cat. no. 160069). 20 uL of a selected Tie2 reference compound was placed in a selected well of the 96-well plate, and diluted 1:4 with 100% DMSO from an initial concentration of about 10 mM to a final concentration of about 2.5 mM, then diluted 1:3 with 100% DMSO for a 10 point dilution to a final concentration of about 0.128 uM.

Test compounds (10 uL of a 10 mM concentration) were similarly diluted 1:4 with 100% DMSO to obtain a sample concentration of about 2.5 mM, then diluted 1:3 for a 10 point dilution to finally obtain a concentration of about 0.128 uM for each test compound. 20 uL of 100% DMSO served as positive controls, while and 10 ul of the 2.5 mM concentration of the reference compound served as the negative control. A 2 uL aliquot from each well (test compounds, positive and negative controls) in the 96-well plate was added to designated wells in the 24-well cell culture plate (1:250). The culture plate was incubated for 2.5 at 37° C. in an atmosphere of about 5% CO2.

The Tie-2 ligand was stimulated with the following series of preparations: (1) about 0.5 mL of a protease inhibitor cocktail (Sigma-Aldrich Co., cat. no. P8340) was thawed; (2) to prepare the phosphatase inhibitor, a 300 mM NaVO4 (Sigma-Aldrich Chem. Co., cat. no. S6508-10G) stock solution in PBS was made and stored at RT. Two 1 ml aliquots of the NaVO4 solution was prepared in separate two vials by adding 100 uL of the NaVO4 stock solution to 900 uL RT PBS and each solution was activated by adding 6 uL of H2O2 to each vial. Both NaVO4 solutions were mixed, wrapped in aluminum foil and stored at RT for 15 min. The Delfia plates, containing 200 uL of PBS+0.1% TWEEN20, were washed three times and blocked by adding 200 uL of a diluted solution of 5% BSA (16 mL of stock 7.5% BSA solution, available from Perkin-Elmer Wallac, Cat. No. CR84-100, was diluted with 8 mL of room temperature PBS). The plates were then stored at room temperature for about one hour.

100 uL of 35% BSA solution was diluted with 3.4 mL of ice cold PBS to make a 1% BSA/PBS solution. 100 uL of this 1% BSA/PBS solution was diluted with 900 uL of ice cold PBS. hAng1 was reconstituted with 250 uL of ice cold PBS+0.1% BSA to make a 100 ug/mL concentration in solution.

The solution was separated into 70 uL aliquots and stored at −80° C.

1 mL of the 30 mM solution of $NaVO_4$/PBS was diluted with 99 mL of ice cold PBS to form a 300 uM concentration. The solution was kept cold on ice. 210 uL of the activated $NaVO_4$ and 280 uL of the protease inhibitor preparation was added to 21 mL of RIPA buffer and kept cold on ice.

Dilute hAng1 and stimulate cells:

70 uL of the 100 ug/mL stock solution was added to 700 uL in 1% BSA/DMEM (1:10) to 10 ug/mL concentration, and it was stored on ice. 5 uL of this 10 ug/mL hAng1 preparation was added to each well of the 24-well plate. The plate was shaken at 700 rpm at 37° C. for about 2.5 minutes.

After shaking, the wells were incubated for 7.5 min at 37° C. The media was removed and 400 uL of ice cold PBS+300 uM $NaVO_4$ was added. The wells were kept on ice for at least 5 min and washed 1× with ice cold PBS+300 uM $NaVO_4$. The wells were tapped against a dry paper towel.

The cells were lysed with 150 uL of RIPA, 300 uM of $NaVO_4$, and 100 uL/1*$10^7$ cells protease inhibitor cocktail (purchased from Sigma-Aldrich, Cat. No. P8340). The solution was incubated, then shaken on ice for 30 min.

The BSA blocking solution was removed from the 96-well plates, which were then tapped dry. 140 uL of cell lysate was added to the antibody-coated plate and the plate was incubated at 4° C. for 2 hours.

Delfia 25× Wash Buffer Concentrate (purchased from Perkin-Elmer Wallac, Cat. No. 1244-114) was diluted with 24 parts DDI water to obtain a washing solution. The lysate was removed and the plate was washed three times each with 400 uL of Delfia washing solution. The plate was tap dried with a paper towel.

The Anti-Phosphotyrosine clone 4G10 (purchased from Upstatebiotech Co., Cat. No. 05-321) was diluted with Delfia Assay Buffer (purchased from Perkin-Elmer Wallac, cat. no. 1244-1111) to make a solution of about 1 ug/mL in concentration. 100 uL of antibody was added to the plate and the plate was incubated at room temperature for one hour.

The plate was again washed three times with 400 uL pretime of the Delfia Washing solution.

The Eu-N1 labeled anti-mouse antibody (purchased from Perkin-Elmer Wallac, cat. no. AD0124) was diluted with Delfia Assay Buffer to make a solution of about 0.1 ug/mL in concentration.

100 uL of antibody was added to the plate and the plate was incubated at room temperature for one hour.

The plate was again washed with Delfia Wash Buffer three times as described above. 100 uL of Delfia Enhancement Solution (purchased from Perkin-Elmer Wallac, Cat. No. 1244-105) was added to each well and the plate was incubated at room temperature for 5 min in the dark.

The Europium signal was measured with a Victor multilabel counter (Wallac Model 1420) while shaking (shake fast, linear, 0.10 mm for 1 s) using a Europium protocol.

Raw data was analyzed using a fit equation in XLFit. $IC_{50}$ values were then determined using Grafit software. Compounds of the invention can be shown to have activity in the Tie-2 delfia cell-based assay.

The compounds of the invention also were found to have inhibitory activity with respect to Aurora kinase enzymes as well. The exemplary assays described as follows were used to make such determination.

Aurora Kinase HTRF Assays

AuroraA-TPX2-Homogeneous Time Resolved Fluorescent (HTRF) Kinase Assay:

The Aurora-A HTRF assay begins with Aurora-A in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The Aurora A HTRF assay comprises 1 µL of compound in 100% DMSO, 20 µL of ATP and biotinylated PLK, and 20 µL of AuroraA-TPX2 KD GST for a final volume of 41 µL. The final concentration of PLK is about 1 µM. The final concentration of ATP is about 1 µM (Km(app)=1 µM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 µL of detection reagent. Detection reagents are as follows: Buffer made of 50 mM Tris, pH 7.5, 100mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

AuroraB-Homogeneous Time Resolved Fluorescent (HTRF) Kinase Assay:

The Aurora B HTRF assay begins with Aurora B in the presence of ATP phosphorylating the biotinylated peptide Histone H3. The reaction incubates for about 90 min. the reaction is quentched by addition of detection reagents, which stop the reaction by diluting out the enzyme and chelating the metals due to the presence of EDTA. After addition, the assay is incubated for about 60 min to allow detection reagents to equilibrate.

The Aurora B HTRF assay comprises 1 μL of compound in 100% DMSO, 20 μL of ATP and biotinylated Histone H3, and 20 μL of Aurora B FL His for a final volume of 41 μL. The final concentration of Histone H3 is 0.1 μM. The final concentration of ATP is 23 μM (Km(app)=23 μM+/−2.6) and the final concentration of Aurora B is 400 μM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-His H3) at a final conc of 0.064 nM.

The assay plate is read in either a Discovery or a RubyStar. The eu-anti-His H3 is excited at 320 nm and emits at 615 nm to excite the SA-APC which in turn emits at 655 nm. The ratio of SA-APC at 655 nm (excited due to close proximity to the Eu-anti-H is H3 because of phosphorylation of the peptide) to free Eu-anti-His H3 at 615 nm will give substrate phosphorylation.

Of the compounds tested, exemplary compounds 23-26 exhibited an average $IC_{50}$ value of 160 nM or less in the human HTRF assay for the inhibition of the Aurora kinase A and B enzymes. Of the compounds tested, exemplary compounds 23 and 25 exhibited an average $IC_{50}$ value of 25 nM or less in the human HTRF assay for the inhibition of the Aurora kinase A and B enzymes.

Indications

In one embodiment of the invention, there is provided a method of modulating Tie-2 and/or Aurora kinase enzyme in a subject, the method comprising administering to the subject an effective dosage amount of a compound of a compound of Formulae I and II.

Accordingly, compounds of the invention are useful for, but not limited to, the prevention or treatment of neoplasia including cancer and metastasis, including, but not limited to: carcinoma such as cancer of the bladder, breast, colon, kidney, liver, lung (including non small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The compounds are useful for the treatment of neoplasia selected from lung cancer, colon cancer and breast cancer.

The compounds would also be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the invention are also useful in the treatment of cardiovascular conditions such as atherosclerosis, restenosis, arteriosclerosis, vascular occlusion and carotid obstructive disease.

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the invention are also useful in the treatment of diabetic conditions such as diabetic retinopathy and microangiopathy.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation, cancer and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable excipients, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art.

The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables. The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulae I and II may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

Alternatively, the compounds of the invention may also be used in co-therapies with other anti-neoplastic agents, such as other kinase inhibitors including p38 inhibitors CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of the Formula I:

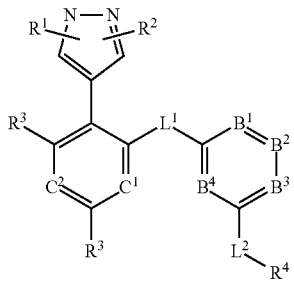

I or a pharmaceutically acceptable salt thereof, wherein
each of $B^1$, $B^2$, $B^3$ and $B^4$, independently, is $CR^3$;
$C^1$ is N;
$C^2$ is $CR^3$;
$L^1$ is $NR^3$, O, S, C(O), S(O), $SO_2$ or $CR^3R^3$;
$L^2$ is —C(O)—, —S(O)$_2$—, —$NR^3$—, —(CR$^3$R$^3$)$_n$C(O)NR$^3$—, —COO—, —(CR$^3$R$^3$)$_n$NR$^3$C(O)—, —(CR$^3$R$^3$)$_n$S(O)$_2$NR$^3$— or —NR$^3$S(O)$_2$—;
$R^1$ is H, $C_{1-10}$-alkyl, $C_{2-10}$-alkenyl, $C_{2-10}$-alkynyl or $C_{3-7}$-cycloalkyl, each of the $C_{1-10}$-alkyl, $C_{2-10}$-alkenyl, $C_{2-10}$-alkynyl or $C_{3-7}$-cycloalkyl optionally substituted with 1-5 substitutents of $R^6$, or $R^1$ is $R^6$;
$R^2$ is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl;
each $R^3$, independently, is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl, the $C_{1-10}$-alkyl optionally substituted with 1-5 substituents of $R^5$ or $R^6$;
$R^4$ is $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally substituted with 1-5 substituents of $R^5$ or $R^6$; or
$R^4$ is a partially or fully saturated or unsaturated 3-8 membered monocyclic, 6-12 membered bicyclic, or 7-14 membered tricyclic carbocyclic or aryl ring system, wherein each ring of said ring system-is optionally substituted independently with 1-3 substituents of $R^5$, $R^6$, oxo, $NR^6R^6$, $OR^6$, $SR^6$, $C(O)R^6$, $COOR^6$, $C(O)NR^6R^6$, $NR^6C(O)R^6$, $NR^6C(O)NR^6R^6$, $OC(O)NR^6R^6$, $S(O)_2R^6$, $S(O)_2NR^6R^6$ or $NR^6S(O)_2R^6$;
$R^5$ is a partially or fully saturated or unsaturated 3-8 membered monocyclic, 6-12 membered bicyclic, or 7-14 membered tricyclic carbocyclic or aryl ring system, wherein each ring of said ring system is optionally substituted independently with 1-3 substituents of $R^6$, oxo, $NR^6R^6$, $OR^6$, $SR^6$, $C(O)R^6$, $COOR^6$, $C(O)NR^6R^6$, $NR^6C(O)R^6$, $NR^6C(O)NR^6R^6$, $OC(O)NR^6R^6$, $S(O)_2R^6$, $S(O)_2NR^6R^6$ or $NR^6S(O)_2R^6$;
each $R^6$, independently, is H, oxo, halo, haloalkyl, CN, OH, $NO_2$, $NH_2$, acetyl, $C_{1-10}$-alkyl, $C_{2-10}$-alkenyl, $C_{2-10}$-alkenyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or ring a saturated or partially or fully unsaturated 3-8 membered monocyclic, 6-12 membered bicyclic, or 7-14 membered tricyclic carbocyclic or aryl ring system, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and
n is 0, 1 or 2.

2. The compound of claim 1, or a pharmaceutically acceptable salt thereof, wherein $L^1$ is $NR^3$, O or S.

3. The compound of claim 1, or a pharmaceutically acceptable salt thereof, wherein $L^2$ is —$NR^1$—, —(CR$^3$R$^3$)$_n$C(O)NR$^3$— or —(CR$^3$R$^3$)$_n$NR$^3$C(O)—.

4. The compound of claim 1, or a pharmaceutically acceptable salt thereof, wherein $R^4$ is phenyl, naphthyl, cyclopropyl, cyclobutyl, cyclopentyl, cyclohexyl and cycloheptyl, each ring of which is optionally substituted independently with one or more substituents of $R^5$ or $R^6$.

5. The compound of claim 1, or a pharmaceutically acceptable salt thereof, wherein
each of $B^1$, $B^2$, $B^3$ and $B^4$, independently, is $CR^3$;
$L^1$ is $NR^3$, O or S;
$L^2$ is —$NR^3$—, —C(O)NR$^3$— or —NR$^3$C(O)—; and
$R^4$ is phenyl, naphthyl, cyclopropyl, cyclobutyl, cyclopentyl, cyclohexyl and cycloheptyl, each ring of which is optionally substituted independently with one or more substituents of $R^5$ or $R^6$.

6. A compound of the Formula II:

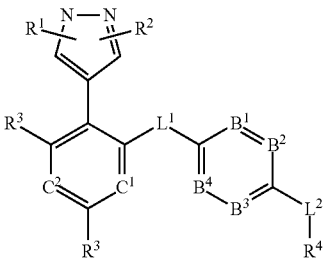

or a pharmaceutically acceptable salt thereof, wherein
each of $B^1$, $B^2$, $B^3$ and $B^4$, independently, is $CR^3$;
$C^1$ is N;
$C^2$ is $CR^3$;
$L^1$ is $NR^3$, O, S, C(O), S(O), $SO_2$ or $CR^3R^3$;
$L^2$ is —C(O)—, —S(O)$_2$—, —$NR^3$—, —($CR^3R^3$)C(O)—$NR^3$—, —COO—, —($CR^3R^3$)$_n$$NR^3$C(O)—, —($CR^3R^3$)S(O)$_2$$NR^3$— or —$NR^3$S(O)$_2$—;
$R^1$ is H, $C_{1-10}$-alkyl, $C_{2-10}$-alkenyl, $C_{2-10}$-alkynyl or $C_{3-7}$-cycloalkyl, each of the $C_{1-10}$-alkyl, $C_{2-10}$-alkenyl, $C_{2-10}$-alkynyl and $C_{3-7}$-cycloalkyl optionally substituted with 1-5 substituents of $R^6$, or $R^1$ is $R^6$;
$R^2$ is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl;
each $R^3$, independently, is H, $C_{1-10}$-alkyl, halo, CN, haloalkyl, $NO_2$, $NH_2$, —NH—$C_{1-10}$-alkyl, —N-di-$C_{1-10}$-alkyl, OH or —O—$C_{1-10}$-alkyl, $C_{1-10}$-alkyl optionally substituted with 1-5 substituents of $R^5$ or $R^6$;
$R^4$ is $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally substituted with 1-5 substituents of $R^5$ or $R^6$; or
$R^4$ is a partially or fully saturated or unsaturated 3-8 membered monocyclic, 6-12 membered bicyclic, or 7-14 membered tricyclic carbocyclic or aryl ring system, wherein each ring of said ring system is optionally substituted independently with 1-3 substituents of $R^5$, $R^6$, oxo, $NR^6R^6$, $OR^6$, $SR^6$, C(O)$R^6$, COOR$^6$, C(O)$NR^6R^6$, $NR^6$C(O)$R^6$, $NR^6$C(O)$NR^6R^6$, OC(O)$NR^6R^6$, S(O)$_2$$R^6$, S(O)$_2$$NR^6R^6$ or $NR^6$S(O)$_2$$R^6$;
$R^5$ is a partially or fully saturated or unsaturated 3-8 membered monocyclic, 6-12 membered bicyclic, or 7-14 membered tricyclic carbocyclic or aryl ring system, wherein each ring of said ring system is optionally substituted independently with 1-3 substituents of $R^6$, oxo, $NR^6R^6$, $OR^6$, $SR^6$, C(O)$R^6$, COOR$^6$, C(O)$NR^6R^6$, $NR^6$C(O)$R^6$, $NR^6$C(O)$NR^6R^6$, OC(O)$NR^6R^6$, S(O)$_2$$R^6$, S(O)$_2$$NR^6R^6$ or $NR^6$S(O)$_2$$R^6$;
each $R^6$, independently, is H, oxo, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic, 6-12 membered bicyclic, or 7-14 membered tricyclic carbocyclic or aryl ring system, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and
n is 0, 1 or 2.

7. The compound of claim 6, or a pharmaceutically acceptable salt thereof, wherein $L^1$ is $NR^3$, O or S.

8. The compound of claim 6, or a pharmaceutically acceptable salt thereof, wherein $L^2$ is —$NR^3$—, —($CR^3R^3$)$_n$C(O)$NR^3$— or —($CR^3R^3$)$_n$$NR^3$C(O)—.

9. The compound of claim 6, or a pharmaceutically acceptable salt thereof, wherein $R^4$ is phenyl, naphthyl, cyclopropyl, cyclobutyl, cyclopentyl, cyclohexyl and cycloheptyl, each ring of which is optionally substituted independently with 1-3 substituents of $R^5$ or $R^6$.

10. The compound of claim 6 wherein
each of B, $B^2$, $B^3$ and $B^4$, independently, is $CR^3$;
$L^1$ is $NR^3$, O or S;
$L^2$ is —$NR^3$—, —C(O)$NR^3$— or —$NR^3$C(O)—; and
$R^4$ is phenyl, naphthyl, cyclopropyl, cyclobutyl, cyclopentyl, cyclohexyl and cycloheptyl, each ring of which is optionally substituted independently with 1-3 substituents of $R^5$ or $R^6$.

11. A pharmaceutical composition comprising a pharmaceutically acceptable excipient and an effective dosage amount of a compound of claim 1.

12. A pharmaceutical composition comprising a pharmaceutically acceptable excipient and an effective dosage amount of a compound of claim 6.

13. The compound of claim 1, or a pharmaceutically acceptable salt thereof, selected from 3-(3-(1H-pyrazol-4-yl)pyridin-2-yloxy)-N-(3-isopropylphenyl)-4-methylbenzamide;
  3-(3-(1-benzyl-1H-pyrazol-4-yl)pyridin-2-yloxy)-N-(3-isopropylphenyl)-4-methylbenzamide;
  3-(3-(1H-pyrazol-4-yl)pyridin-2-yloxy)-N-(5-cyclohexyl-2-methoxyphenyl)-4-methylbenzamide;
  3-(3-(1H-pyrazol-5-yl)pyridin-2-yloxy)-4-methyl-N-(3-(trifluoromethyl)phenyl)benzamide;
  N-(4-(3-(1H-pyrazol-4-yl)pyridin-2-yloxy)phenyl)-2-(phenylamino)benzamide;
  N-(4-(3-(1H-pyrazol-4-yl)pyridin-2-yloxy)phenyl)-3-(trifluoromethyl)benzamide; and
  N-(4-(3 -(3-amino-1H-pyrazol-4-yl)pyridin-2-yloxy)phenyl)-2-(phenylamino)benzamide.

* * * * *